United States Patent [19]
Parton

[11] Patent Number: 5,905,038
[45] Date of Patent: May 18, 1999

[54] FILTRATION AND CULTURE METHODS AND APPARATUS

[75] Inventor: Adrian Parton, Exning, United Kingdom

[73] Assignee: Severn Trent Water Limited, Birmingham, United Kingdom

[21] Appl. No.: 08/976,953

[22] Filed: Nov. 24, 1997

Related U.S. Application Data

[63] Continuation of application No. PCT/GB96/01239, May 23, 1996.

[30] Foreign Application Priority Data

May 25, 1995 [GB] United Kingdom .................... 9510634

[51] Int. Cl.$^6$ ................. C12M 1/12; C12Q 1/24
[52] U.S. Cl. ................... 435/287.6; 435/287.7; 435/287.9; 435/297.5; 435/308.1; 435/261; 435/30; 422/101; 436/177
[58] Field of Search ................. 435/30, 34, 810, 435/39, 287.1, 287.6, 261, 287.7, 287.8, 287.9, 308.1, 297.1, 297.2, 297.5; 422/101; 210/406, 445, 446, 450, 455, 474, 482, 321.75, 321.84; 73/863.23, 863.25; 436/177

[56] References Cited

U.S. PATENT DOCUMENTS

| | | |
|---|---|---|
| 2,672,431 | 3/1954 | Goetz . |
| 2,761,813 | 9/1956 | Goetz . |
| 2,923,669 | 2/1960 | Poitras . |
| 3,741,877 | 6/1973 | Shaufus et al. . |
| 3,843,452 | 10/1974 | Freake et al. . |
| 3,929,583 | 12/1975 | Sharpe et al. . |
| 4,299,921 | 11/1981 | Youssef . |
| 4,485,171 | 11/1984 | Ikeda et al. . |
| 4,829,005 | 5/1989 | Friedman et al. . |
| 5,202,262 | 4/1993 | Lemonnier . |
| 5,308,483 | 5/1994 | Sklar et al. . |
| 5,360,722 | 11/1994 | Inoue et al. . |

FOREIGN PATENT DOCUMENTS

| | | |
|---|---|---|
| 0 150 775 | 8/1985 | European Pat. Off. . |
| 0 359 249 | 3/1990 | European Pat. Off. . |
| 0 450 850 | 10/1991 | European Pat. Off. . |
| 6-113817 | 4/1994 | Japan . |
| 91/18085 | 11/1991 | WIPO . |

*Primary Examiner*—William H. Beisner
*Attorney, Agent, or Firm*—Pillsbury Madison & Sutro LLP

[57] ABSTRACT

A method and apparatus for filtering microorganisms from a sample and culturing the microorganisms employs a membrane filter (3) in a filter holder (10) in which holder the membrane filter is supported on an absorbent support (26) which is maintained in an expansible compressed state against the membrane filter so that any expansion of the membrane filter when wetted by a sample does not cause bubbling of the membrane filter away from its support entrapping air bubbles and so preventing supply of nutrient from culture medium supplied to the support from reaching the microorganisms on the membrane filter.

12 Claims, 2 Drawing Sheets

FILTRATION AND CULTURE METHODS AND APPARATUS

This is a Continuation of International Appln. No. PCT/GB96/01239 filed May 23, 1996 which desingnated the U.S.

BACKGROUND OF THE INVENTION

1. Field of the Invention

The present invention relates to methods and apparatus for the filtration of micro-organisms from a sample and the culture of the micro-organisms in situ on the filter used in the filtration.

2. Description of the Related Art

As discussed in EP0150775, it is known to capture micro-organisms for culture by the membrane filtration of a sample through a sterile membrane placed on a porous holder. After filtration the membrane may be removed and deposited on to a gelatinous culture medium contained in a Petri dish. The Petri dish may then be incubated at a suitable temperature for the time necessary for the micro-organisms to be able to develop and multiply sufficiently to form colonies visible to the naked eye to permit them to be identified and counted.

Even slightly contaminated samples may be evaluated as the micro-organisms are concentrated on the membrane, and it is possible to filter a significant volume of sample to collect a sufficient number of micro-organisms. However, disadvantages which arise in this method are first that the colonies can run out of nutrients in the local area of the agar medium, which in circumstances where there are large numbers of bacteria on the membrane can result in suppression of growth of individual colonies. Also, care must be exercised in placing the membrane filter on the culture medium to avoid entrapping any air bubbles between the culture medium and the membrane which would prevent contact between the culture medium and a portion of the surface of the membrane, thereby opposing diffusion of the culture medium and inhibiting micro-organism development.

In an alternative procedure, it has been proposed to place the membrane containing the filtered bacteria on to a filter paper wick to conduct nutrient medium to the membrane. However, the amount of medium added to the wick has to be carefully controlled in order that the membrane filter does not become too moist such that confluent growth is observed rather than the growth of individual colonies.

Also, these techniques generally involve the transfer of the membrane from the filtration apparatus to the culturing operation and this additional step has the potential to introduce contamination as the membrane is exposed to the air. It also means that culturing cannot start until the samples have travelled from the sampling site to the laboratory, which take a period of several hours.

As further disclosed in EP-B-0150775, it has been proposed to remedy some of these inconveniences by the use of apparatus consisting of a sterile box with circular elements nested into one another and a removable cover. The box includes an inlet and an outlet disposed on both sides of a holder on which an absorbent pad and a filtration membrane lie, clamped at the periphery of the holder by one of the circular elements. After filtration, a culture medium is introduced through the outlet, that is counter currently to the filtration operation, to saturate the absorbent pad. The box can be placed in an incubator to permit the collected micro-organisms to develop. This avoids the need for any transfer operation after filtration and before culturing and permits samples to be directly taken on the site at which the liquid is collected. However, as stated in EP-B0150775, this method still has serious draw-backs. In particular, the membrane diameter increases when the membrane becomes wetted and since the membrane and the absorbent pad, which are clamped at their periphery to the sterile box, are kept dry prior to use, upon filtration of the sample the wetting of the pad and the membrane may cause the membrane filter to part from the absorbent pad. This will prevent contact between the membrane and the pad saturated with the culture medium and thus disturb the development of the micro-organisms upon incubation.

EP-B0150775 proposes an elaborate solution to this problem which involves sealing a membrane filter across the bottom of a tubular holder such that the holder can be pressurised with air to bulge the membrane outwardly prior to mating it against the surface of a gelled nutrient medium in a cup. This reintroduces the danger of contamination of the system during the manipulation involved. Any micro-organism contamination of the interface between the nutrient medium and the filter membrane is likely to interfere with the growth of the micro-organisms on the opposite face of the membrane filter. Furthermore, the apparatus depicted in EP-B0150775 is unduly elaborate and cumbersome to manufacture and to use.

We have now appreciated that the problem outlined in EP-B0150775 is capable of a substantially simpler solution which avoids reintroducing the draw-backs inherent in the earlier prior art.

Accordingly, the present invention now provides a method for filtering micro-organisms from a sample and culturing the micro-organisms, which method comprises filtering a sample containing micro-organisms through a membrane filter in a filter holder in which holder the membrane filter is supported on an absorbent support, and then supplying culture medium to the micro-organisms on the membrane filter in the filter holder by absorbing the medium into the absorbent support, characterised in that the absorbent support is maintained in an expansible compressed state against the membrane filter.

By virtue of the absorbent support being compressed against the membrane filter, if expansion of the membrane filter takes place any tendency of the membrane filter to expand away from the absorbent support is countered by the absorbent support being able to expand and maintain contact with the membrane filter.

There is therefore no need to remove the membrane filter from the absorbent support after the filtration operation and to mate the surface of the membrane filter against a gel of nutrient medium. Instead, sterile nutrient medium may be applied directly to the compressed absorbent support in the filter holder.

The absorbent support is preferably of reticulated foam. Suitable polymer foams are available made from a wide variety of plastics materials such as polyethers, polyesters, polypropylene, polyvinylchloride and polyurethanes. Preferred polymer foams are of from 50 to 200 ppi (pores per inch) (equivalent to 20 to 80 pores per centimeter) e.g. Approximately 100 ppi (equivalent to 40 pores per centimeter).

Suitably, the absorbent support takes the form of a block of such reticulated foam having a free uncompressed thickness of 0.5 to 3 cm, e.g. about 1 cm and presenting a major face on which the membrane filter may be placed directly or, more preferably, with a layer of a wick material such as filter paper between the membrane filter and the absorbent support.

Preferably, the absorbent support is compressed to a is thickness of from ⅞ths to ¹⁄₁₀th of its free uncompressed thickness. The degree of compression need not be uniform over the whole area of the absorbent support. For instance, if the compression is actually applied at the edges of the absorbent support, the compression in the centre of the absorbent support may well be significantly less.

Preferably, between the membrane filter and the absorbent support of reticulated foam there is an intermediate compression spreading support layer transmitting compression forces applied to the edges of the assembly of the membrane filter, compression spreading layer and absorbent support of reticulated foam so that the centre of the assembly is also under compression. Such a compression spreading layer may conveniently be provided by a sheet of filter paper. Other suitable materials may be employed. They should preferably be flexible and porous. Preferably, such a compression spreading material also serves as a wick to draw culture medium from the absorbent support and to supply it to the membrane filter. It should not obstruct expansion of the absorbent support to match expansion of the membrane filter. It may be chosen to expand as much as the membrane filter when wetted.

A liquid sample to be filtered can be placed in a sample chamber above the membrane filter and can be drawn through the membrane filter by suitable means such as a vacuum pump or syringe. The filtered liquid will be withdrawn through an outlet from the filter holder. Preferably, the culture medium is supplied to the absorbent support for the membrane filter through this same outlet. To facilitate this, the apparatus may be inverted at this stage. Preferably, the culture medium is initially contained in a sealed container in which it can be maintained in a sterile condition and the container of culture medium is connected to the outlet of the filter holder prior to the seal being broken to release the culture medium on to the absorbent support.

The invention includes apparatus for use in filtering and culturing micro-organisms comprising a filter holder defining a flow-path for fluid to be filtered, a filter member in said flow-path comprising a membrane filter supported on an absorbent support, and means compressing said absorbent support against the membrane filter.

Preferably, the filter holder may comprise telescopically interfitting first and second sections, said first section having a floor containing an outlet for filtered fluid and a peripheral wall, said membrane filter and said absorbent support therefore being received in said first section on said floor with said membrane filter further away from said floor, and said second section of the filter holder being received in said first section and compressing said membrane filter and said absorbent support against said floor.

The outlet in the floor of the first section of the filter holder may be bridged by a porous support surface underlying the absorbent support of the membrane filter.

Suitably, the outlet in the floor of the first section of the filter holder is adapted for connection to a syringe by a standard syringe fitting.

The apparatus further includes an assay kit comprising apparatus as described above together with a container of sterile liquid culture medium for introduction on to the absorbent support.

Preferably, said container of culture medium is adapted to mate with the outlet of the first section of the filter holder to allow introduction of the culture medium therethrough on to the absorbent support.

Preferably, means are provided at the outlet of the first section of the filter holder for co-operating with the seal of the container of culture medium to break said seal and release the culture medium after a connection has been established between the container of culture medium and the filter holder.

BRIEF DESCRIPTION OF THE DRAWINGS

The invention will be further described and illustrated with reference to the accompanying drawings in which.

DETAILED DESCRIPTION OF THE INVENTION

Figure 1:
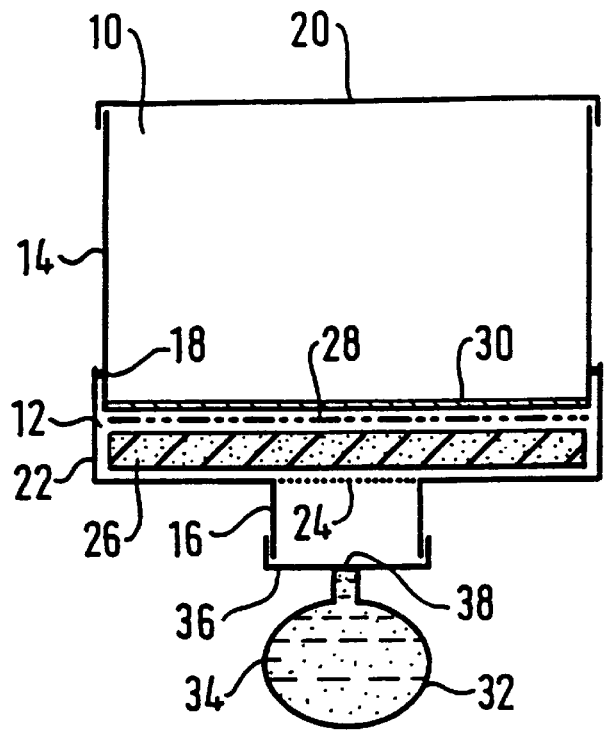
FIG. 1 is a schematic longitudinal section through apparatus according to the invention.

As shown in FIG. 1, a typical apparatus according to the invention comprises a filter holder 10 having a first section 12 and second section 14 interfitting therewith. Both are preferably of circular cross-section transverse to the plane of the drawing. The first section 12 is in the form of a tray having in its base a centrally located outlet 16 and having an upstanding peripheral wall 22 within which is received the cylindrical second section 14 sealed thereto by an O-ring seal 18. A lid 20 is provided for the second section 14.

Within the filter holder there is a positioned a first layer of support material such as plastics scrim 24. Alternatively, the neck of the outlet 16 may be bridged by support material located in the outlet 16 such as a porous plastics plug or spider. Above the support scrim 24 is a pad of reticulated absorbent foam 26 which acts as a support for the membrane filter described hereafter. Above the reticulated foam 26 is a layer of filter paper 28 and above that is a membrane filter 30 itself. The assembly of the reticulated foam 26, filter paper wick 28 and membrane filter 30 is compressed by the bottom edge of the second section 14 of the filter holder 10. The reticulated foam pad may for instance have a 1 cm uncompressed thickness and at the edge of the assembly may be compressed down to say 3 mm. The compression is spread across the centre of the reticulated foam pad principally by the membrane filter but also by the filter paper layer 28 so that in the centre the compression would typically be somewhat less than at the edge, e.g. to 5 mm. The amount of compression applied will generally not be critical. Provided there is some compression, then if there is expansion of the membrane filter during use, the foam pad 26 can expand to accommodate it and maintain contact between the filter paper 28 and the membrane filter 30.

For completeness, FIG. 1 also illustrates the presence of a container 32 in the form of a bulb of liquid culture medium 34 attached by a suitable connector schematically shown at 36 to the outlet 16. In use however, the bulb 32 would not normally be attached to the filter holder 10 at this stage. In place of a flexible bulb containing the culture medium, one might suitable employ a sealed ampoule or closed syringe. Preferably however, whatever form of container is employed will be sealed by a seal 38 which is frangible after the container has been connected to the outlet 16 in a sealing manner. Where the container 32 is a flexible bulb, the seal may be adapted to be burst simply by applying external pressure to the bulb. Alternatively, the connection between the outlet 16 and the connector 36 may be designed such that as the connection is fully made, mechanical means perforates the seal 38. To this end, one could for instance provide a bayonet type lock between the container 32 and the outlet 16 such that after the two have been brought into engagement, the container 32 could be rotated to a position in which it is allowed to be pushed toward the filter holder 10 causing the seal 38 to be ruptured against a pin or other perforating member located in the connector.

Figure 2:
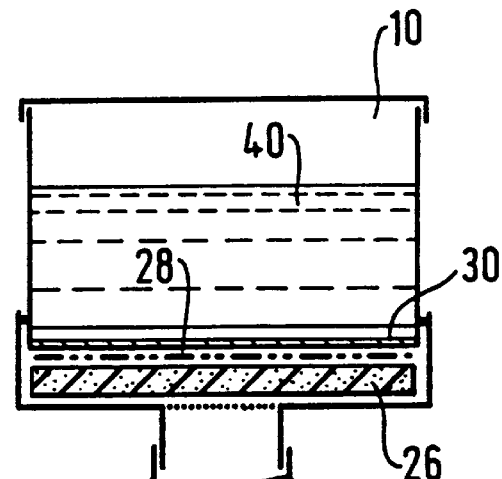
FIG. 2 is a view similar to FIG. 1 of the apparatus in use during the filtration of a sample.
Figure 3:
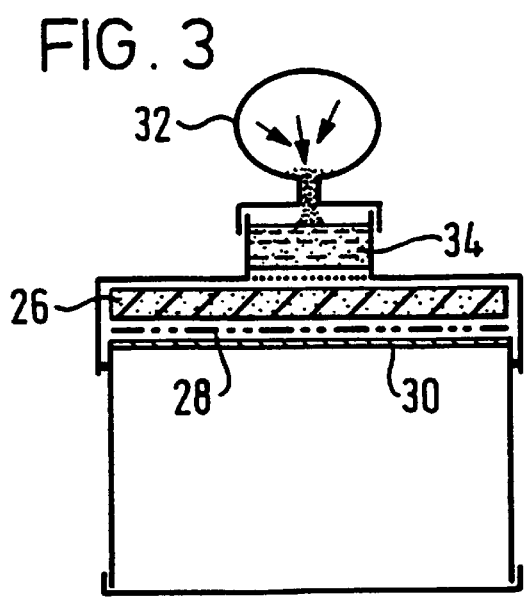
FIG. 3 is a similar view of the apparatus during the introduction of culture medium on to the absorbent support therein.

The use of the apparatus of FIG. 1 is illustrated in FIGS. 2 and 3. In a first phase, a sample of liquid 40 is introduced into the filter holder 10 and the lid 20 is applied to prevent contamination from the air. Using a syringe 42, the liquid sample is sucked through the filter assembly 26, 28, 30 depositing micro-organisms from the liquid sample on to the upper surface of the membrane filter 30. The apparatus is then inverted as shown in FIG. 3 and the container 32 of culture medium is put into position and its seal 38 is ruptured to release the culture medium 34 on to the absorbent foam 26 from where it is supplied by a wicking action by the paper layer 28 to the membrane filter 30.

The apparatus may then be incubated at a suitable temperature to produce micro-organism growth.

The apparatus described is of simple construction and lends itself to use in the field. For instance, a sample of water taken from a river, reservoir, storage tank or other such source may be placed directly into the filter holder 10 and filtered at the time of sampling. The culture medium may be applied immediately and the culturing process may be initiated. It may take several hours for the sample to be returned to the laboratory at which further work on the sample takes place but the transport time is not wasted. Rather it is used for the culturing of the organisms.

Figure 5:
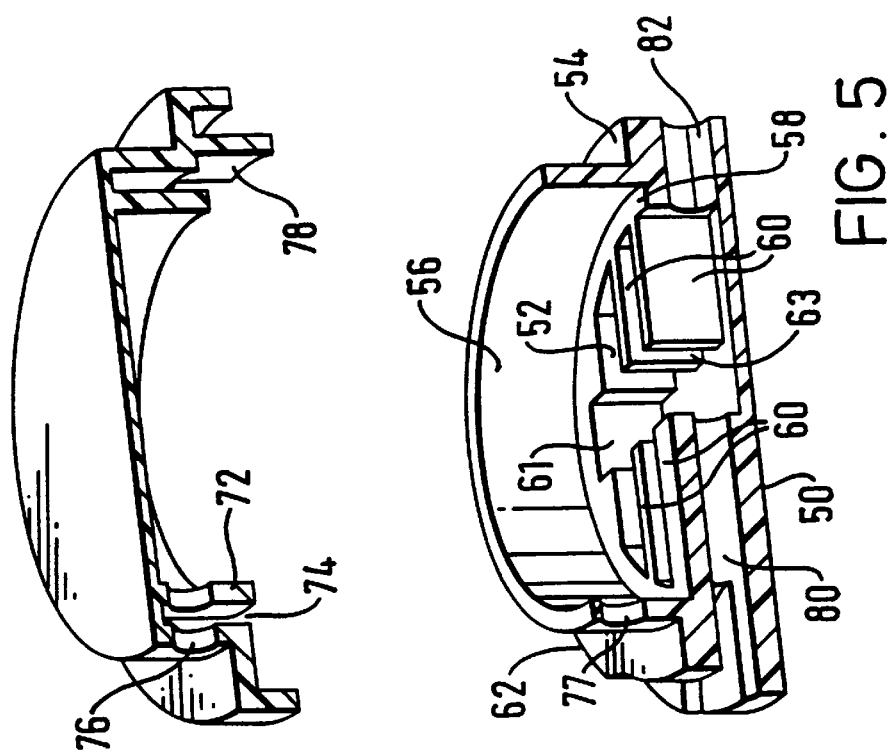
FIG. 5 is a similar view but with both the lid and the body portion cut through on a diameter.
Figure 4:
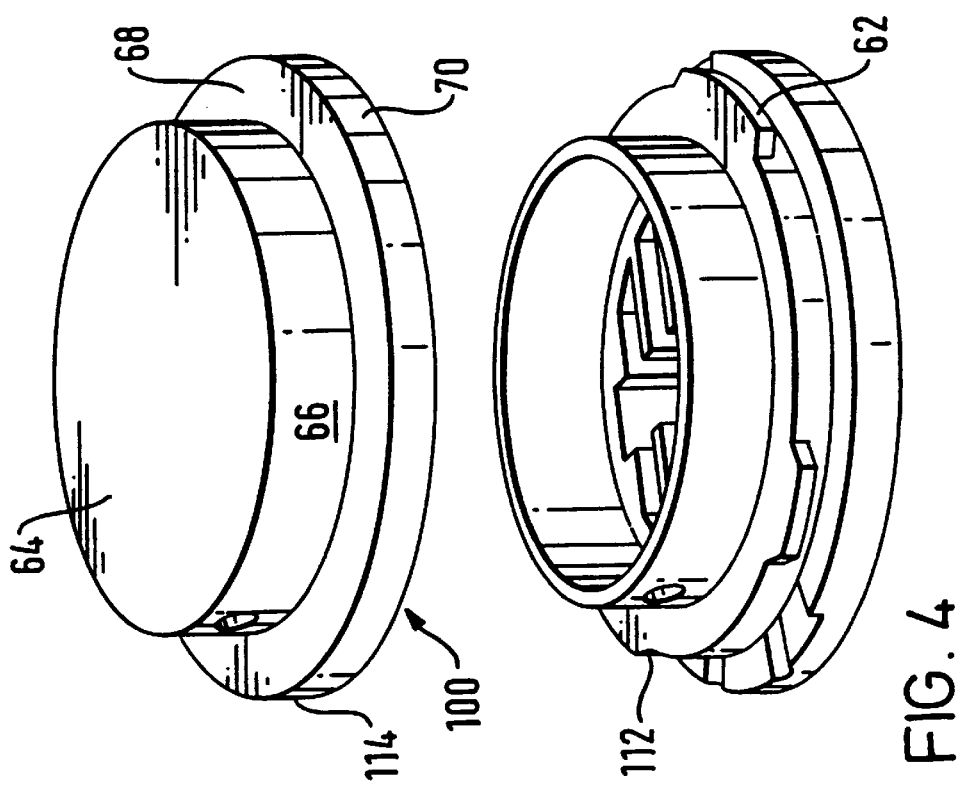
FIG. 4 shows a second embodiment according to the invention in a perspective view with body and lid portions of the apparatus separated.

The alternative embodiment shown (with some features omitted for clarity) in FIGS. 4 and 5 is similar in functionality, although different in form. It comprises a filter holder 100 having a lid portion 114 and a body portion 112. Body portion 112 is a plastics integral molding having a circular base plate So from which rises a generally circular wall 52 defining a well. A generally circular flange 54 extends radially outward from the top of the well and carries a cylindrical wall 56 upstanding therefrom. A radially inward portion of the upper surface of the flange 54 forms a ledge 58 for receiving the edge of a filter assembly (not shown) and walls 60 upstanding from the base plate 50 provide support for more central portions of the filter assembly but leave a central channel 61 between their ends 63. The upper surfaces of walls 60 and the lege 58 of flange 54 define a floor on which the filter assembly is received.

Bayonet fitting lugs 62 project radially outward at intervals from the edge of the flange 54.

The lid portion 114 is an integral plastics molding comprising a circular top plate 64 from which depends a cylindrical wall 66 terminating in a radially extending circular flange 68 which bears a further cylindrical wall 70. Within the cylindrical wall 66 is a smaller diameter cylindrical wall 72 spaced therefrom by an annular gap 74 adapted to receive wall 56 of the body portion 112. Lugs for co-operating with bayonet lugs 62 are provided on the interior of wall 70. A through aperture 76 pierces both walls 66 and 72. A depending shield wall 78 is provided on the underside of flange 68, approximately opposite aperture 76.

A circular cross-section bore 80 pierces through wall 52 of the body portion 112 below and parallel to the flange 54 and a similar bore 82 is provided directly opposite.

In use, a filter assembly comprising the scrim 24, reticulated foam 26, filter paper 28 and membrane filter 30 described in connection with FIGS. 1 to 3 is placed on the ledge 58 within the wall 56 after a cylindrical vial containing culture medium is placed in the channel 61.

When the lid position 114 is fitted, the bottom of wall 72 presses on the edge of the filter assembly as described in connection with FIGS. 1 to 3.

The bayonet lugs 62 secure the lid portion to the body portion but allow some twisting movement of one relative to the other whereby aperture 76 may be brought into and out of alignment with a similar aperture 77 in wall 56 and to bring shield wall 78 into and out of a blocking position in relation to bore 82.

Lastly, a chisel member (not shown) is inserted into bore 80 to abut the vial of culture medium. The chisel may have a cylindrical body portion and a pointed end abutting the vial. The sharpened end may be of any desired shape. The cylindrical portion may be a push fit in the bore 80 or may be a threaded engagement with the bore.

A sample to be investigated is introduced via apertures 76, 77, e.g. from a syringe and is passed through the filter assembly to exit via bore 82. Thereafter, the lid and body portions are twisted to close aperture 76 and to bring wall 78 into a blocking position closing bore 82. The chisel is then pressed home (e.g. by turning it if it is threaded) to break the culture medium vial. The culture medium impregnates the foam of the filter assembly and culturing of any trapped micro-organisms commences. The apparatus may be inverted during culturing. After culturing, one may observe micro-organisms through the lid portion and, if desired, the apparatus may be disassembled and the cultured microorganisms may be investigated further.

The ability to close off the inlet and outlet bores 76, 77 and 82 by rotation of the lid provides a convenient way to exclude contamination during culturing incubation whilst permitting some air access. Also, the apparatus is adapted to be prepared well in advance and to be packed fully assembled in a sterile manner for storage prior to use.

The use of the apparatus may be illustrated by the following examples:

EXAMPLE 1

100 ml of water spiked with *E.coli* was filtered through the unit described above in relation to FIGS. 1 to 3. A number of such units were prepared in this way. Each unit was inverted and at various volumes and strengths of nutrient broth were allowed to soak into the foam base of each unit. Units were incubated at 37° C. overnight and micro-organism counts as follows were obtained:

| Nutrient Broth added | Replicate 1 | Replicate 2 |
| --- | --- | --- |
| 5ml × 2X | 24 | 25 |
| 7ml × 2X | 27 | 27 |
| 3ml of 2X | 27 | 30 |
| 5ml × 1X | 41 | 25 |

EXAMPLE 2

100 ml of river water diluted in dechlorinated tap water was filter through each of a number of units described above. Various amounts and strengths of membrane lauryl broth (Oxoid) were added to the inverted units to soak into the foam support of each unit. Incubation was conducted overnight at 37° C. and yellow colonies were recorded as presumptive coliforms. The membrane filter from one unit was moved and placed on solidified medium as a control. The micro-organism counts were as follows:

| Lauryl sulphate added | Replicate 1 | Replicate 2 |
|---|---|---|
| Agar control | 47 | 37 |
| 4ml × 0.5X | 41 | 71 |
| 4ml 1X | 54 | 60 |
| 4ml of 1.5X | 37 | 51 |

EXAMPLE 3

100 ml volumes of *E.coli* seeded water samples were filtered through units of the kind described above. Each unit was inverted and 2 ml of 1.3X strength membrane lauryl sulphate broth containing the chromogen BCIG was added to the foam. The broth was made up according to Sartory and Howard but used 39 mg of BCIG/100 ml rather than 20 mg/100 ml. Control membranes were transferred after filtration to MLGA (Sartory et al). Incubation was conducted for 4 hours at 30° C. and 14 hours at 37° C. both green and yellow colonies were counted as follows:

| Sample No. | Control (agar plate) Green | Control (agar plate) Yellow | Foam Pad Green | Foam Pad Yellow |
|---|---|---|---|---|
| 1 | 0 | 1 | 0 | 0 |
| 2 | 20 | 0 | 17 | 0 |
| 3 | 34 | 0 | 20 | 0 |
| 4 | 10 | 21 | 28 | 29 |
| 5 | 0 | 0 | 0 | 0 |
| 6 | 0 | 18 | 0 | 10 |
| 7 | 0 | 17 | 0 | 22 |
| 8 | 22 | 0 | 20 | 0 |
| 9 | 17 | 0 | 16 | 0 |
| 10 | 0 | 10 | 0 | 17 |

In summary it can be concluded that there is no statistically significant difference between the number of organisms recovered on the agar plate or foam pad system. Thus proving that the foam pad system is comparable for agar plates even when more complex growth media i.e. inclusion of chromogens are used in the system.

Whilst the invention has been described with reference to the specific embodiment illustrated, many variations and modifications thereof are possible within the scope of the invention.

I claim:

1. A method for filtering micro-organisms from a sample and culturing the micro-organisms, said method comprising:

filtering a sample containing micro-organisms through a membrane filter in a filter holder in which holder the membrane filter is supported on an absorbent support, and then supplying culture medium to the micro-organisms on the membrane filter in the filter holder by absorbing the medium into the absorbent support, wherein the absorbent support is maintained in an expansible compressed state against the membrane filter where the micro-organisms are filtered and cultured.

2. A method as claimed in claim 1, wherein the absorbent support is of reticulated foam.

3. A method as claimed in claim 1 or claim 2, wherein said absorbent support is compressed to a thickness of from ⅞ths to 1/10th of its free uncompressed thickness.

4. A method as claimed in claim 3, wherein said culture medium is contained initially in a sealed container which is connected to said filter holder in communication with said absorbent support prior to said seal being broken to release said culture medium onto said absorbent support.

5. A method as claimed in claims 1 or 2, wherein said culture medium is contained initially in a sealed container (32) which is connected to said filter holder in communication with said absorbent support prior to said seal being broken to release said culture medium onto said absorbent support.

6. Apparatus for use in filtering and culturing micro-organisms comprising:

a filter holder defining a flow path for fluid to be filtered, and a filter member in said flow path comprising a membrane filter supported on an absorbent support said absorbent support being compressed against the membrane filter where the micro-organisms are filtered and cultured.

7. Apparatus as claimed in claim 6, wherein said filter holder comprises telescopically interfitting first and second sections, said first section having a floor communicating with an outlet for filtered fluid and a peripheral wall, said membrane filter and said absorbent support therefor being received in said first section on said floor with said membrane filter further away from said floor, and said second section of the filter holder having a portion received in said first section and compressing said membrane filter and said absorbent support against said floor.

8. A culturing kit comprising apparatus as claimed in claim 6 or claim 7, together with a container of sterile, liquid culture medium for introduction onto said absorbent support.

9. A culturing kit as claimed in claim 8, wherein said filter holder comprises telescopically interfitting first and second sections, said first section having a floor communicating with an outlet for filtered fluid and a peripheral wall, said membrane filter and said absorbent support therefor being received in said first section on said floor with said membrane filter further away from said floor and said second section of the filter holder having a portion received in said first section and compressing said membrane filter and said absorbent support against said floor, and wherein said container of culture medium is adapted to mate with said outlet of the first section of the filter holder to allow introduction of said culture medium therethrough onto said absorbent support.

10. A culturing kit as claimed in claim 8, wherein said culture medium is contained in a closed container within said apparatus and means are provided in the apparatus operable from outside said apparatus for breaching said container to release said culture medium.

11. An apparatus for filtering and culturing micro-organisms, said apparatus comprising:

a filter holder providing a flow path through which fluid containing the micro-organisms can flow; and a filtering assembly positioned such that the fluid flowing through said flow path flows through said filtering assembly;

said filtering assembly comprising a membrane filter and an absorbent support, said membrane filter filtering the micro-organisms from the fluid flowing through said filtering assembly such that the micro-organisms contained in the fluid are deposited on a portion of the membrane filter;

wherein said membrane filter becomes wet with the fluid so that said portion thereof having the micro-organisms deposited thereon expands and moves in a direction away from said absorbent support member and said absorbent support member is compressed against said membrane filter such that said absorbent support member remains engaged with said portion of said membrane filter having the micro-organisms deposited thereon during said movement thereof in the direction away from said absorbent support member.

12. A culturing kit comprising:

a container containing sterile, liquid culturing medium;

an apparatus for filtering and culturing micro-organisms, said apparatus comprising:
- a filter holder providing a flow path through which fluid containing the micro-organisms can flow; and
- a filtering assembly positioned such that the micro-organisms containing the fluid flowing through said flow path flows through said filtering assembly;
- said filtering assembly comprising a membrane filter and an absorbent support, said membrane filter filtering the micro-organisms from the fluid flowing through said filtration assembly such that the micro-organisms are deposited on a portion of said membrane filter;
- wherein said membrane filter becomes wet with the fluid so that said portion thereof having the micro-organisms deposited thereon moves in a direction away from said absorbent support member and said absorbent support member is compressed against said membrane filter such that said absorbent support member remains engaged with said portion of said membrane filter having the micro-organisms deposited thereon during said movement thereof in the direction away from said absorbent support member, said container being communicable with said absorbent support member such that, after the micro-organisms have been filtered from the fluid by said membrane filter, the sterile, liquid culturing medium can be introduced to said absorbent support member.

* * * * *